United States Patent
Garcia et al.

(10) Patent No.: US 6,863,093 B2
(45) Date of Patent: Mar. 8, 2005

(54) METHOD OF FILLING A RESERVOIR WITH FLUID, A FLUID-FILLER SYSTEM, AND A FILLER SOURCE

(75) Inventors: Firmin Garcia, Evreux (FR); Jean-Paul Lecoutre, Breteuil sur Iton (FR)

(73) Assignee: Valois Sas, Le Neubourg (FR)

( * ) Notice: Subject to any disclaimer, the term of this patent is extended or adjusted under 35 U.S.C. 154(b) by 0 days.

(21) Appl. No.: 10/832,241

(22) Filed: Apr. 27, 2004

(65) Prior Publication Data

US 2004/0211481 A1 Oct. 28, 2004

(30) Foreign Application Priority Data

Apr. 28, 2003 (FR) .............................................. 03 05158

(51) Int. Cl.⁷ ................................................. B65B 1/04
(52) U.S. Cl. ................................ 141/2; 141/18; 141/21; 141/27
(58) Field of Search .......................... 141/2, 18, 21–27, 141/67

(56) References Cited

U.S. PATENT DOCUMENTS

| | | | |
|---|---|---|---|
| 3,343,718 A | * 9/1967 | Siegel et al. | .................... 222/1 |
| 3,444,906 A | 5/1969 | Moonan et al. | |
| 3,620,266 A | 11/1971 | Ryder | |
| 3,853,157 A | * 12/1974 | Madaio | ......................... 141/2 |

FOREIGN PATENT DOCUMENTS

EP     0 440 477 A     8/1991

* cited by examiner

*Primary Examiner*—Steven O. Douglas
(74) *Attorney, Agent, or Firm*—Sughrue Mion, PLLC

(57) ABSTRACT

The present invention proposes a system and a method for filling a reservoir with fluid, on which system there is mounted a dispenser member. An external fluid source is connected to the dispenser member, and the fluid in the source is sucked into the empty reservoir by the suction which exists in the reservoir after it has been emptied by the dispenser member.

15 Claims, 7 Drawing Sheets

METHOD OF FILLING A RESERVOIR WITH FLUID, A FLUID-FILLER SYSTEM, AND A FILLER SOURCE

BACKGROUND OF THE INVENTION

The present invention relates to a method, to an external filler source, and to a system for filling a reservoir with a fluid, a liquid, a paste, or even a powder. The dispenser system comprises a fluid dispenser that is essentially constituted by a fluid reservoir designed to contain fluid, and a dispenser member such as a pump mounted in an opening of the fluid reservoir so as to be able to extract fluid therefrom and dispense it through a dispenser head, which advantageously presents a dispenser orifice in which the fluid can be collected or sprayed. This type of fluid dispenser is frequently used in the fields of perfumery, cosmetics, or even pharmacy. These are manual dispensers that the user can hold in one hand via the reservoir of the dispenser, and can press, e.g. by means of the index finger, on a pusher enabling the pump to be actuated, and thus enabling fluid to be dispensed.

The present invention applies more particularly to the dispenser presenting a rigid reservoir having a volume that does not vary. The reservoir can be made of a plastics material, of glass, or even of metal. The dispenser member, namely the pump, is generally fixed on the reservoir by means of a fixing ring. To this end, the reservoir generally forms a neck defining an opening in which the pump is fixed. The present invention also applies more particularly to a certain type of pump, frequently known as an "airless" pump, which functions without taking in air, i.e. the volume of fluid extracted by the pump from the non-deformable reservoir is not replaced by an equivalent volume of outside air. Consequently, each time the pump is actuated, the pressure inside the reservoir reduces, so as to reach a maximum degree of suction when the reservoir contains no more fluid.

In general, when this particular type of "airless" dispenser is empty, it is destined to be discarded.

OBJECT AND SUMMARY OF THE INVENTION

The object of the present invention is to define a method of filling this type of dispenser without having to remove the pump from the reservoir. Another object of the invention is to define a filler source and a dispensing and filler system, enabling this type of dispenser to be filled without having to remove the pump.

To do this, the present invention proposes a method comprising:

a prior step of emptying the reservoir by using the pump to extract the fluid so that suction is created in the reservoir;

a step of supplying fluid externally, said step consisting in supplying the outlet channel with fluid coming from an external source; and an opening step consisting in opening the outlet valve, while holding the inlet valve open, so that the suction existing in the reservoir sucks fluid from the source through the outlet channel, the open outlet valve, the pump chamber, and the open inlet valve, and into the reservoir.

The fluid coming from the external source is advantageously supplied to the outlet channel at a pressure that is substantially equal to or less than atmospheric pressure.

Thus, the method of the invention consists in filling a dispenser reservoir at reduced pressure by sucking in fluid through the pump by opening the outlet and inlet valves.

The invention also proposes an external fluid-filler source for a fluid dispenser, said dispenser comprising:

a reservoir designed to contain a fluid at a pressure that is substantially equal to or less than atmospheric pressure; and a pump associated, in sealed manner, with the reservoir, so as to extract fluid from the reservoir, the pump being of the airless type so that the pressure inside the reservoir reduces as the amount of fluid extracted by the pump increases, said pump including an inlet valve and an outlet valve, the inlet valve communicating with the reservoir, and the outlet valve communicating with an outlet channel, the inlet valve communicating with the outlet valve via a pump chamber, the external fluid-filler source comprising:

a supply of fluid;

a fluid-supplying orifice designed to be connected to the outlet channel of the dispenser;

a supply valve disposed between the supply and the supply orifice, said supply valve being urged into its open position when the supply orifice is connected to the outlet channel of the dispenser, said supply valve including a movable member bearing selectively in leaktight manner on a valve seat. Advantageously, the fluid contained in the supply of the source is at a pressure that is substantially equal to or slightly less than atmospheric pressure, so that the fluid coming from the supply orifice is sucked into the reservoir of the dispenser by the suction which exists therein.

In another aspect of the invention, the source includes opening means that are capable of opening the outlet valve of the dispenser. Advantageously, the opening means also co-operate with the supply valve so as to open it before opening the outlet valve. The opening means preferably comprise a pin defining a connection end secured to the movable member, and a free end for thrust purposes designed to be engaged in the outlet channel of the dispenser so as to open the outlet valve. It is preferable for the pin firstly to open the supply valve so as to enable the fluid coming from the fluid supply to pass into the outlet channel as far as the outlet valve. The outlet valve can then be opened in such a manner as to suck the fluid coming from the supply through the open supply valve. If the outlet valve is opened first, then the suction would force the supply valve into its closed position.

According to another advantageous characteristic of the invention, the outlet channel of the dispenser is formed by an actuator rod that is axially displaceable in a pump body, the rod supporting a piston that is capable of varying the working volume of the pump chamber, the external source then including blocking means so as to block the actuator rod relative to the pump body. The blocking means advantageously include at least two hinged jaws between which the actuator rod is designed to be held in clamped manner. The blocking means preferably include a lever system that is capable of exerting traction which urges the rod out from the body, while said rod is already being held by the jaws. In a practical embodiment, the blocking means include at least two hinged arms, each presenting a fixed end and a jaw-forming free end, the jaws being disposed in such a manner as to define a central housing of size that varies as the jaws are displaced by pivoting the arms, each of the arms also forming a bearing surface designed to come into bearing contact on a fixed element of the dispenser, pivoting the arms in the direction for reducing the size of the central housing, while the rod is inserted in said housing, causes the jaws to clamp onto the rod, and brings the bearing surfaces into contact with the fixed element in such a manner as to exert traction on the rod by means of the jaws, urging the rod out from the body. In practice, it has been found that it is practically essential to hold the actuator rod while the outlet valve is being opened by the pin. Opening the outlet valve tends to displace the actuator rod towards the inside of the pump body under the effect of the suction which exists inside the reservoir. In addition, the lever system enables the actuator rod to be raised very slightly out from the pump body, thereby increasing the flow passage for fluid through the open inlet and outlet valves.

In a practical aspect of the invention, the external source may be constituted by another fluid dispenser also including a reservoir and a pump. By way of example, the source may be in the form of a dispenser presenting a reservoir of medium to large capacity and having an end wall that is equipped with opening and blocking means. The dispenser to be filled may have a reservoir of small capacity that needs to be refilled frequently. For an identical fluid, the dispensing and filler system makes it possible to have a domestic dispenser of large capacity, and a travel dispenser of small capacity.

In a practical embodiment, the inlet valve comprises a valve seat and a movable member, and the outlet valve comprises a valve seat and a movable member, the movable members being formed by a valve part so that the movable members are constrained to move together, it thus being possible to open the inlet and outlet valves simultaneously. This type of pump enables an airless dispenser reservoir to be emptied completely while creating a relatively large amount of suction. The suction is used for filling by means of the external source.

The invention also provides a dispenser and filler system comprising: a fluid dispenser comprising a reservoir designed to contain a fluid at a pressure that is substantially equal to or less than atmospheric pressure, and a pump associated, in sealed manner, with the reservoir, so as to extract fluid from the reservoir, the pump being of the airless type so that the pressure inside the reservoir reduces as the amount of fluid extracted by the pump increases, said pump including an inlet valve and an outlet valve, the inlet valve communicating with the reservoir, and the outlet valve communicating with an outlet channel, the inlet valve communicating with the outlet valve via a pump chamber; and an external filler source as defined above.

BRIEF DESCRIPTION OF THE DRAWINGS

The invention is described in greater detail below with reference to the accompanying drawings, showing, by way of non-limiting example, an embodiment of the invention.

In the figures.

MORE DETAILED DESCRIPTION

Figure 1:
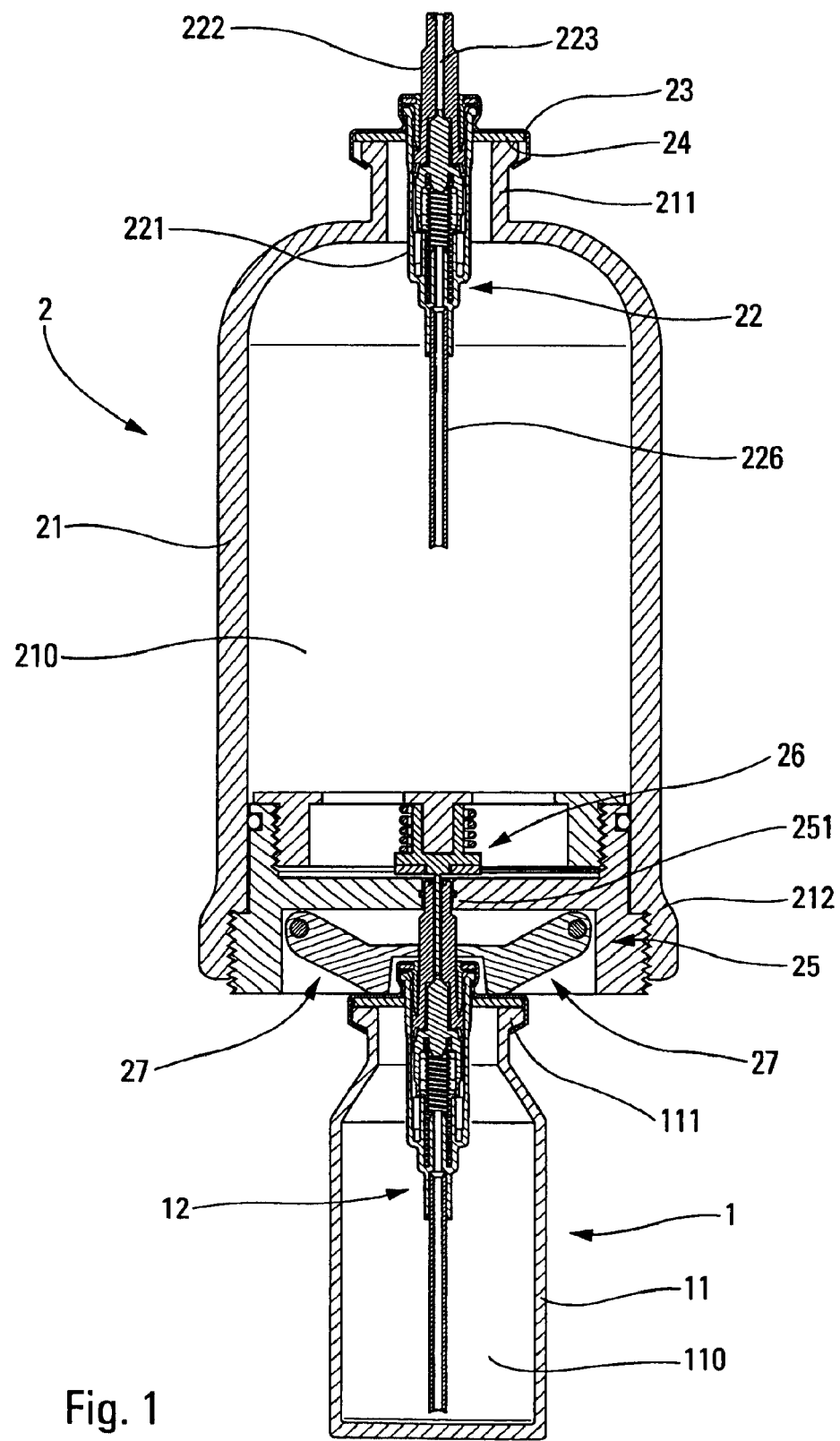
FIG. 1 is a vertical cross-section view through a fluid dispenser and filler system of the invention.

The method and the reservoir filler source of the invention apply to a particular fluid dispenser which is described first in detail below. The dispenser, shown in most of the figures, is designated overall by numerical reference 1.

The fluid dispenser 1 essentially comprises a receptacle 11, and a dispenser member 12, which, in this case, is a pump. Indeed, throughout this description, the dispenser member is always referred to as a pump. The receptacle 11 is a rigid-wall receptacle which can be made of glass, of a plastics material, of metal, or of any other rigid material. The receptacle comprises an end wall, a side wall, and a neck 111 which defines an opening giving access to the inside of the receptacle. The internal volume defined inside the receptacle serves as a fluid reservoir 110 designed to contain a fluid such as perfume, a lotion, or more generally any perfumery, cosmetic, or even pharmaceutical fluid. Given that the receptacle 11 is rigid, the fluid reservoir 110 defines a determined fixed capacity.

Figure 2A:
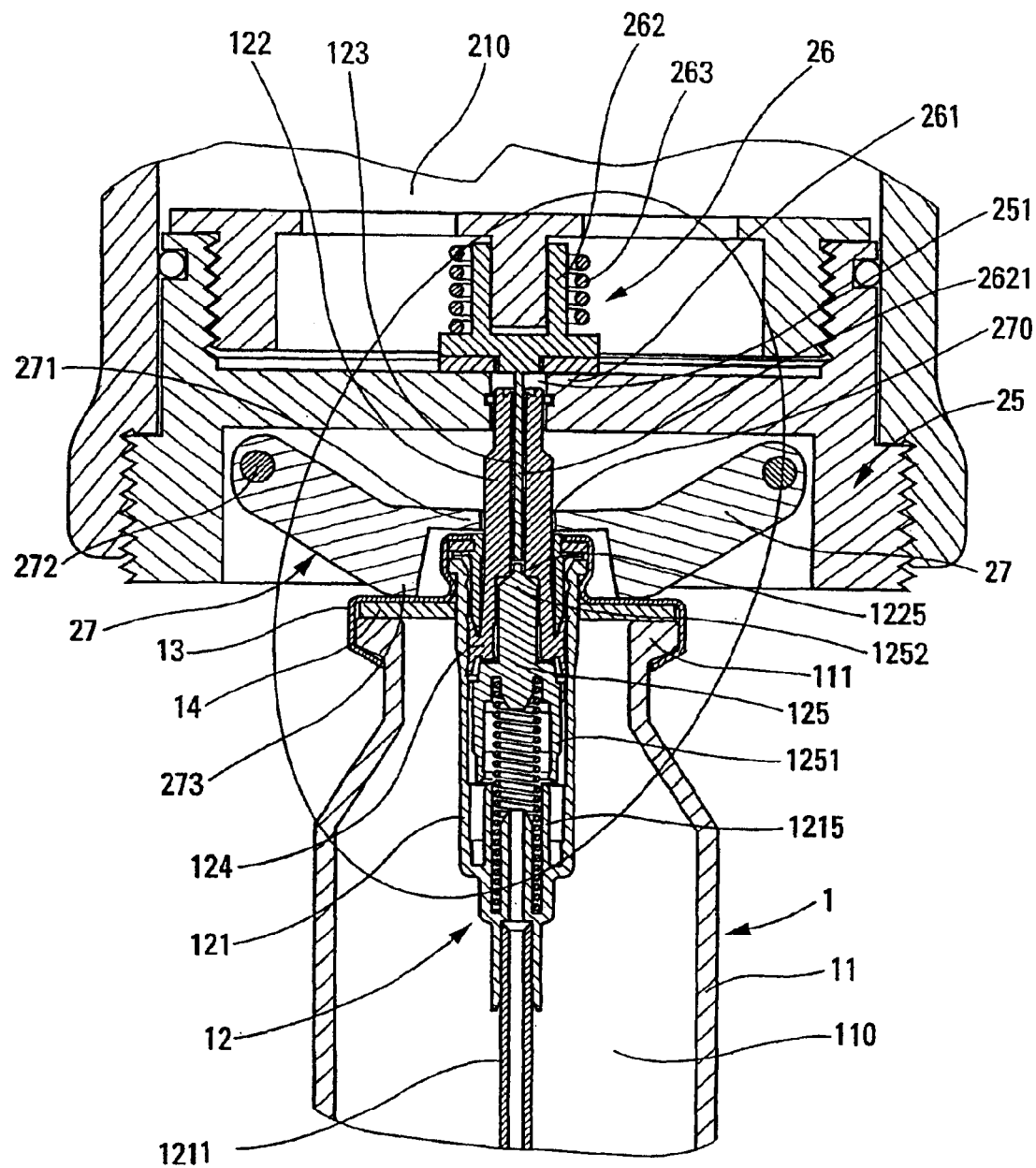
FIGS. 2a and 2b are respectively large-scale and very large-scale views of a portion of the FIG. 1 system in the rest position.
Figure 2B:
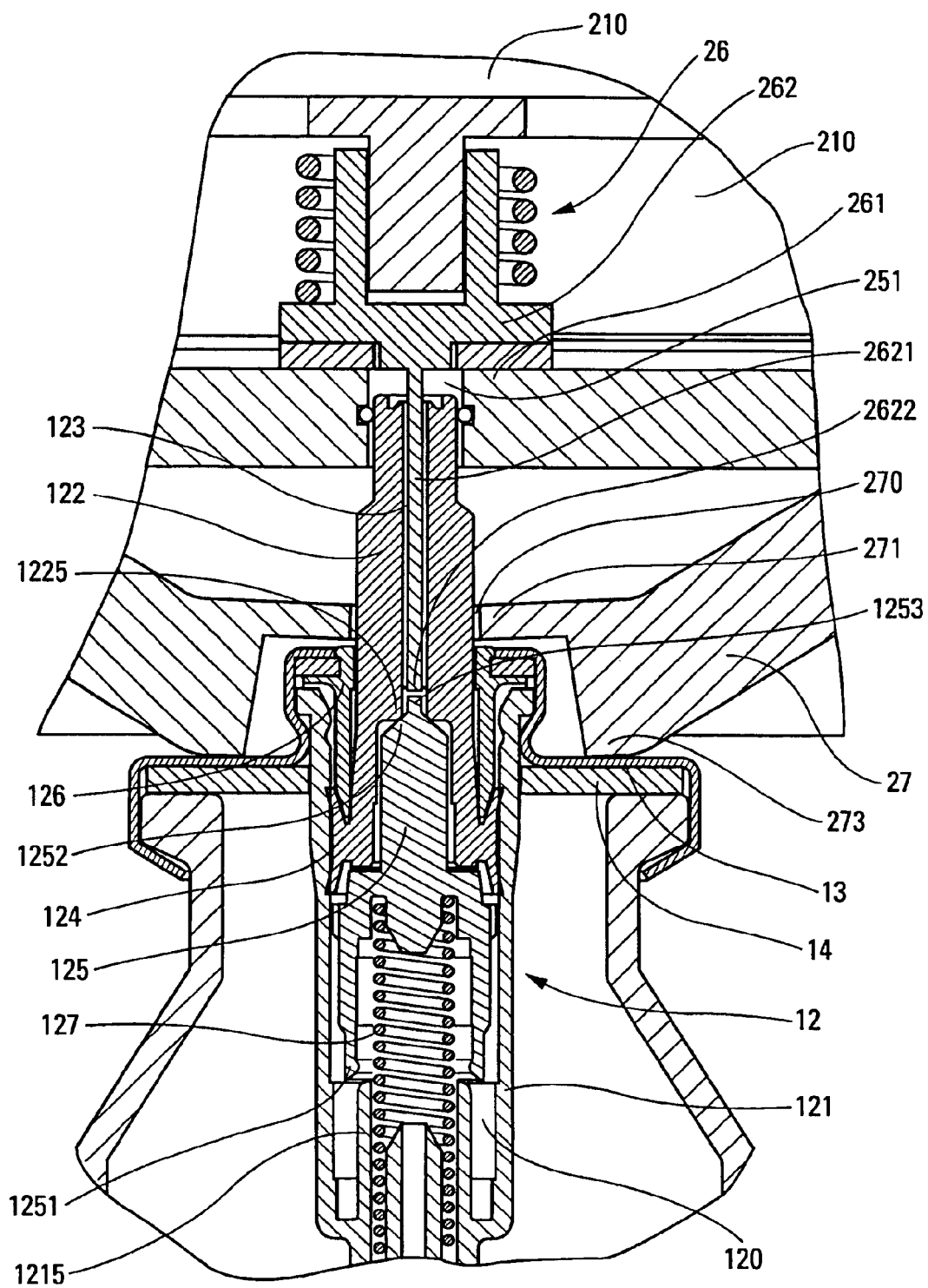

The pump 12, shown in FIG. 1, and seen more clearly still in FIGS. 2a and 2b, is a conventional, manual, precompression pump. The pump is of the "airless" type, i.e. without an air inlet, so that the quantity of fluid that it extracts is not replaced by a corresponding volume of outside air. The consequences for the dispenser, and more particularly for the reservoir 110, are described below. The pump 12 comprises a pump body 121 defining an inlet that is advantageously provided with a dip tube 1211. The inside of the pump body 121 defines a cylinder for slidably receiving a piston 124. In this case, the piston 124 is secured to an actuator rod 122 having an outlet channel 123 formed therein. In this case, the piston 124 and the actuator rod 122 are made integrally as a single piece. In this case, the actuator rod 122 also forms an outlet-valve seat 1225 situated at the bottom end of the outlet channel 123. The pump further comprises a valve part 125 engaged in the pump body 121. The valve part 125 is urged against the actuator rod 122 by a return and precompression spring 127. The spring 127 acts in such a manner as to push the valve part 125 and the actuator rod 122 out of the pump body 121 via its top end remote from its inlet. In order to hold the actuator rod 122 and the valve part 125 inside the pump body, a ferrule 126 is provided, force-fitted in the pump body and serving as an abutment for the actuator rod and the valve part when the pump is in its rest position. By way of example, the ferrule 126 can come into abutment against the piston 124. The valve part 125 defines two movable valve members, namely a movable outlet-valve member 1252 and a movable inlet-valve member 1251. The valve part 125 forms a valve pin defining a frustoconical surface 1252 designed to come into leaktight contact with the valve seat 1225 formed by the actuator rod 122. The frustoconical surface 1252 is urged against the seat 1225 by the force exerted by the spring 127. The frustoconical surface 1252 is extended so as to form a tip 1253 that is engaged inside the outlet channel 123 at its bottom end. The valve part 125 also forms a skirt having a free end that forms a bead 1251 designed to come into leaktight sliding contact with the outside of a tube 1215 formed by the pump body 121 substantially at its inlet. The spring 127 is engaged inside said tube 1215. The tube 1215 acts as an inlet-valve seat, whereas the bead formed at the bottom end of the skirt forms the movable inlet-valve member 1251. In the rest position shown in FIGS. 2a and 2b, the spring 127, which bears on the valve part 125, urges the valve part 125 against the actuator rod 122, which is itself urged against the ferrule 126 that is force-fitted in the pump body 121. The outlet valve formed by the seat 1225 and the movable member 1252 is closed, whereas the inlet valve formed by the bead 1251 and the tube 1215 is open. By pressing on the actuator rod 122 in such as a manner as to drive it into the pump body 121, the piston 124 slides in sealed manner in the cylinder of the body and pushes the valve part 125 downwards against the action of the spring 127. It will easily be understood that after a short stroke, the bead 1251 becomes engaged in leaktight manner around the tube 1215. A volume is thus isolated from the outside by the closed outlet valve and from the inside of the reservoir 110 by the closed inlet valve. This volume constitutes a pump chamber 120. By continuing to press on the rod 122, the piston 124 continues to descend inside the cylinder of the body, thereby resulting in a reduction in the working volume of the pump chamber 120. The pressure inside the chamber increases until it overcomes the force exerted by the spring 127. The inlet valve thus opens lifting the frustoconical surface off the seat 1225. A passage is thus freed for the fluid under pressure inside the pump chamber 120, which fluid can flow through the outlet channel 123. The inlet valve is still closed by the engagement of the bead 1251 in leaktight sliding contact around the tube 1215.

To actuate the pump, an actuator head (not shown) is provided, which can be in the form of a pusher forming an outlet duct opening out in a dispenser orifice, advantageously enabling the fluid to be sprayed. With one or more fingers, the user presses on the pusher, so as to drive the actuator rod into the body and thus trigger the process described above. The actuator head is not shown in the figures, given that the head must be removed in order to fill the dispenser 1. The user can remove the actuator head very easily, merely by pulling on it. The actuator head can also be put back in place very simply, since it suffices to force the pusher onto the top end of the actuator rod.

The pump 12 is engaged and held in the neck 111 of the receptacle 11 by means of a crimping ring 13. By way of example, the crimping ring becomes engaged with the pump at the top end of the body 121, e.g. by gripping the ferrule 126. Thus, the crimping ring 13 also contributes to fixing the ferrule 126 permanently in the pump body 121. The crimping ring 13 is crimped around the neck 111, which advantageously forms an outwardly-projecting rim. In order to guarantee sealing at the neck, an annular neck gasket 14 is advantageously provided and is pressed on the top end of the neck by the crimping ring 13. In this way, the reservoir 110 is completely isolated from the outside. Given that the pump 12 is of the airless type, the fluid extracted and dispensed by actuating the pump has the effect of reducing the remaining volume of fluid stored in the reservoir 110, whereas the total volume of the reservoir remains fixed. As a result, the pressure inside the reservoir 110 reduces, so as to reach a maximum level of suction when the reservoir contains no more fluid. Given that the fixing of the pump on the receptacle is leaktight, said suction persists inside the reservoir. Normally, the dispenser would then be discarded.

The spirit of the present invention is to use the suction inside the reservoir 110 to refill the dispenser through the pump 12. This method can be implemented with any dispenser comprising a rigid receptacle and an "airless" pump fixed on top in leaktight manner. The particular type of pump described above constitutes a non-limiting example of one pump amongst others.

The present invention also makes use of an external source, which, in this case, is designated overall by numerical reference 2. The external source 2 and the dispenser 1 form a filler system of the invention. The external source 2 can be presented in very different forms. It can be in the form of a simple fluid supply specially dedicated to filling the fluid dispenser 1. The external source can thus be a filler fountain, e.g. installed in shops so that users can come and refill their empty fluid dispensers having reduced inside pressure. The external source can also be in the form of another fluid dispenser similar to the dispenser 1. This is the case for the external source 2 shown in the figures. In reality, the external source is a fluid dispenser 2 also including a receptacle 21, defining, internally, a fluid reservoir 210 which serves as a filler supply for the dispenser 1. The receptacle includes a neck 211 in which there is mounted a pump 22, or more generally a fluid dispenser member. The pump 22 can be of a type that is identical to, similar to, or even completely different from the pump of the dispenser 1. The neck can also be provided merely with a stopper. By way of example, the volume of the reservoir 210 can be of a capacity that is greater than or much greater than the capacity of the reservoir 110. Thus, the fluid supply constituted by the reservoir 210 enables the reservoir 110 of the dispenser 1 to be filled several times. The source dispenser 2 includes a bottom end wall 212 equipped with a filler unit that is described in detail below. The unit is designed to co-operate with the dispenser 1 so as to fill its empty reservoir that is itself at a reduced internal pressure.

The fluid stored in the reservoir 210 is at a pressure that is substantially equal to or less than atmospheric pressure. In any case, the pressure does not need to be significantly greater than atmospheric pressure.

The unit includes a base plate 25 which is engaged in sealed manner in the bottom wall 212 of the receptacle 21. In reality, the base plate 25 constitutes the bottom wall of the reservoir 210. The base plate 25 defines a supply orifice 251 which passes through the base plate 25. Consequently, said orifice constitutes a passage providing communication between the inside of the reservoir 210 and the outside. The plate 25 supports a supply valve 26 which enables the supply orifice 251 to be closed selectively. The supply valve 26 includes a movable supply-valve member 262 designed to come selectively into leaktight contact with a supply-valve seat 261. The seat 261 can be formed by the annular peripheral edge of the supply orifice 251 facing the inside of the reservoir 210. The movable member 262 can be urged resiliently by a spring 263 against the seat 261. Thus, the supply orifice 251 can be supplied with fluid from the reservoir 210 only when the movable member 262 is disengaged from or lifted off its seat 261. As a result of the fluid not being under pressure inside the reservoir 210, accidental opening of the valve 26 does not cause a major leak. The movable member 262 also includes a pin 2621 which extends axially through the supply orifice 251. The pin 2621 has a free end for thrust purposes.

The filler unit optionally, but advantageously includes blocking means 27 housed in a housing formed by the base plate 25. The blocking means 27 enable the actuator rod 122 to be blocked relative to the pump body 121 and, as a result, relative to the receptacle 11. The purpose is to prevent the actuator rod 122 from being displaced towards the inside of the body during the filling operation. In this case, the blocking means 27 comprise two hinged arms 27, but it is perfectly possible to provide more arms, e.g. 3, 4, 5, 6, or even more. Each arm is pivotally mounted about a pivot pin 272 secured to the base plate 25. Each arm 27 further comprises a jaw 271 designed to become engaged with the outside wall of the actuator rod 122. The jaws of the arms 27 together form a central internal housing 270 having a size that varies as a function of the pivoting of the arms 27. The central housing 270 can thus shrink so that the jaws 271 become clamped all around the actuator rod 122. However, in the rest position, as shown in FIGS. 2a and 2b, the central housing 270 presents a size, or more precisely an inside diameter, that is greater than the outside diameter of the actuator rod 122. In contrast, when the arms 27 pivot upwards, the inside diameter of the central housing 270 is reduced such that the jaws 271 become clamped around the rod 122. According to another advantageous characteristic, the blocking means 27 include cam or lever means which, in this case, are in the form of a bearing surface 273 designed to come into sliding engagement with a fixed element of the dispenser, which, in this case, is a portion of the crimping ring 13. The purpose of the lever system is to cause the jaws 271, once they are clamped around the rod 122, to exert light upward traction. Because of the particular disposition of the jaw 271, of the pivot pin 272, and of the bearing surface 273, it will easily be understood that upward pivoting of the arm firstly has the effect of bringing the jaw 271 into contact with the rod 122 as a result of the central housing shrinking, and also has the effect of increasing the axial distance which separates the jaw 271 from the bearing surface 273. In other words, the jaw 271 moves axially away from the bearing surface 273 when the arms 27 pivot upwards. This vertical or axial distancing of the jaws 271 has the effect of exerting upward traction on the actuator rod 122.

With the structure of the filler system of the invention described in detail above, there follows a description of a complete operating cycle, describing all the steps of the filling method of the invention.

Reference is made firstly to FIGS. 2a and 2b. The actuator rod 122 is already engaged between the jaws 271, in the central housing 270. The pin 2621 is engaged in the outlet channel 123. However, its thrust end 2622 is not yet in contact with the tip 1253 of the valve part 125. The bearing surfaces 273 are already in contact with the crimping ring 13. In addition, the top end of the actuator rod 122 is already partially engaged in sealed manner in the supply orifice 251. The jaws 271 are not yet clamped around the rod 122.

Figure 3A:
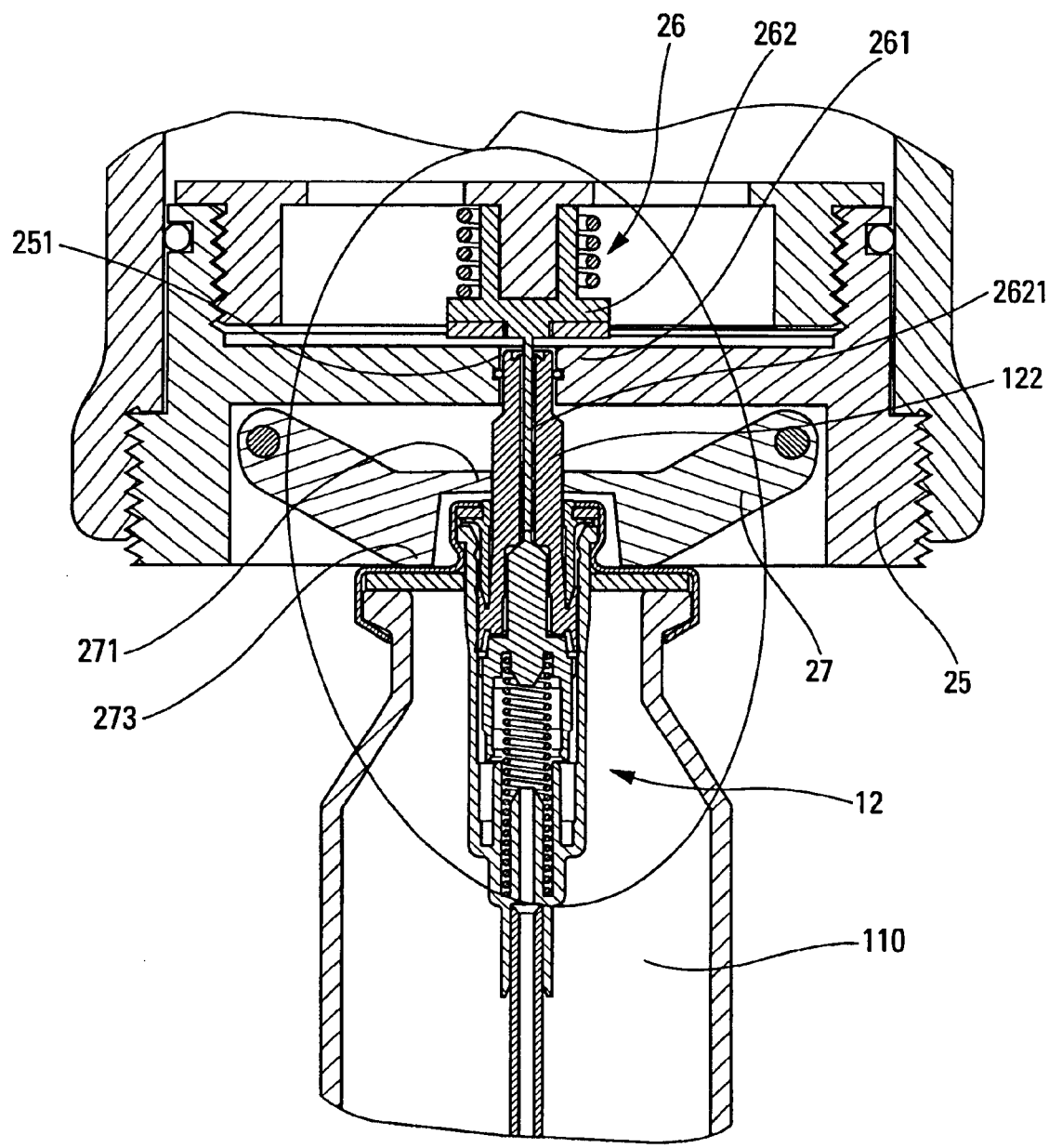
FIGS. 3a and 3b are views similar to FIGS. 2a and 2b just before the filling step.
Figure 3B:
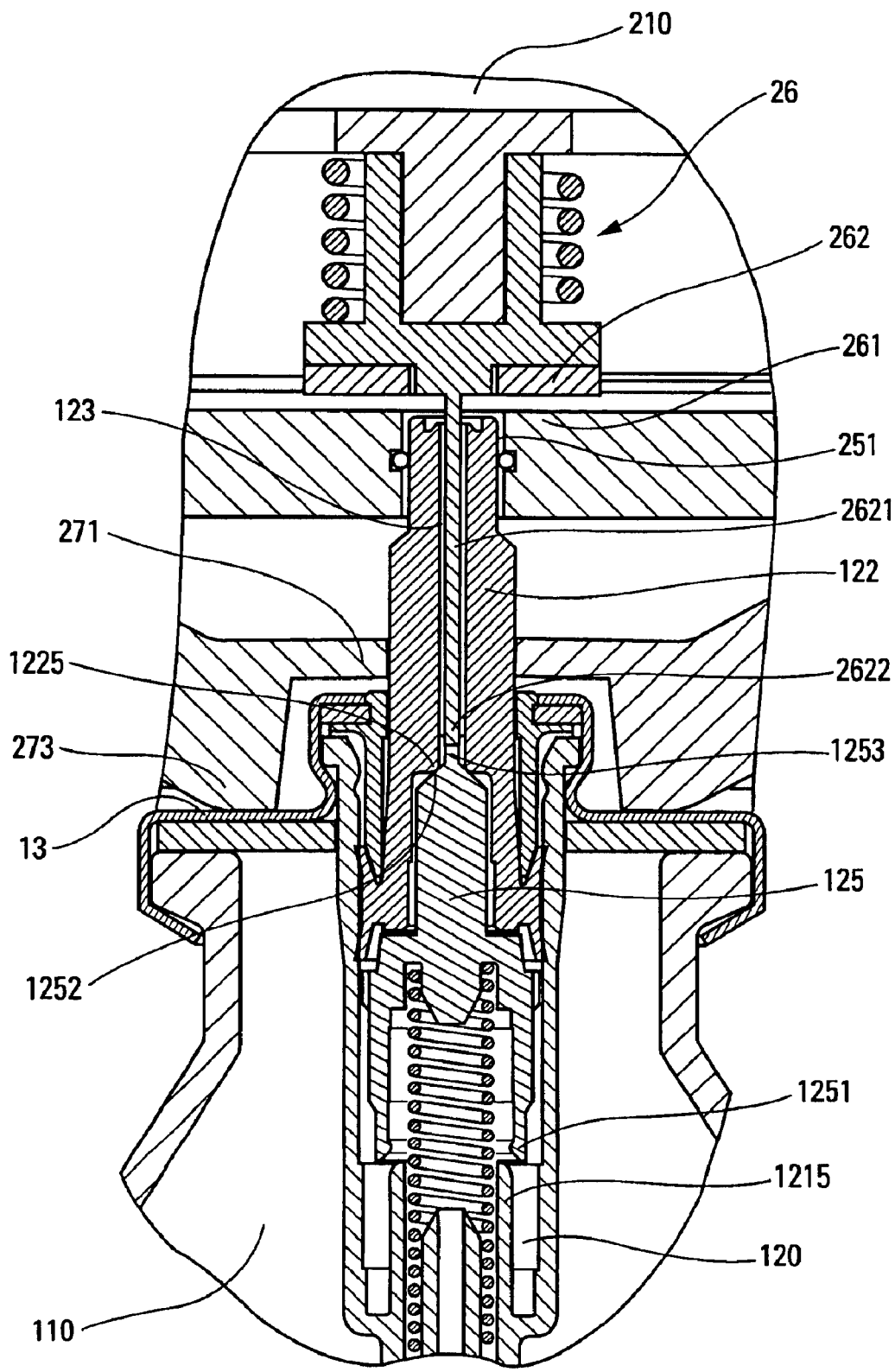
Figure 4A:
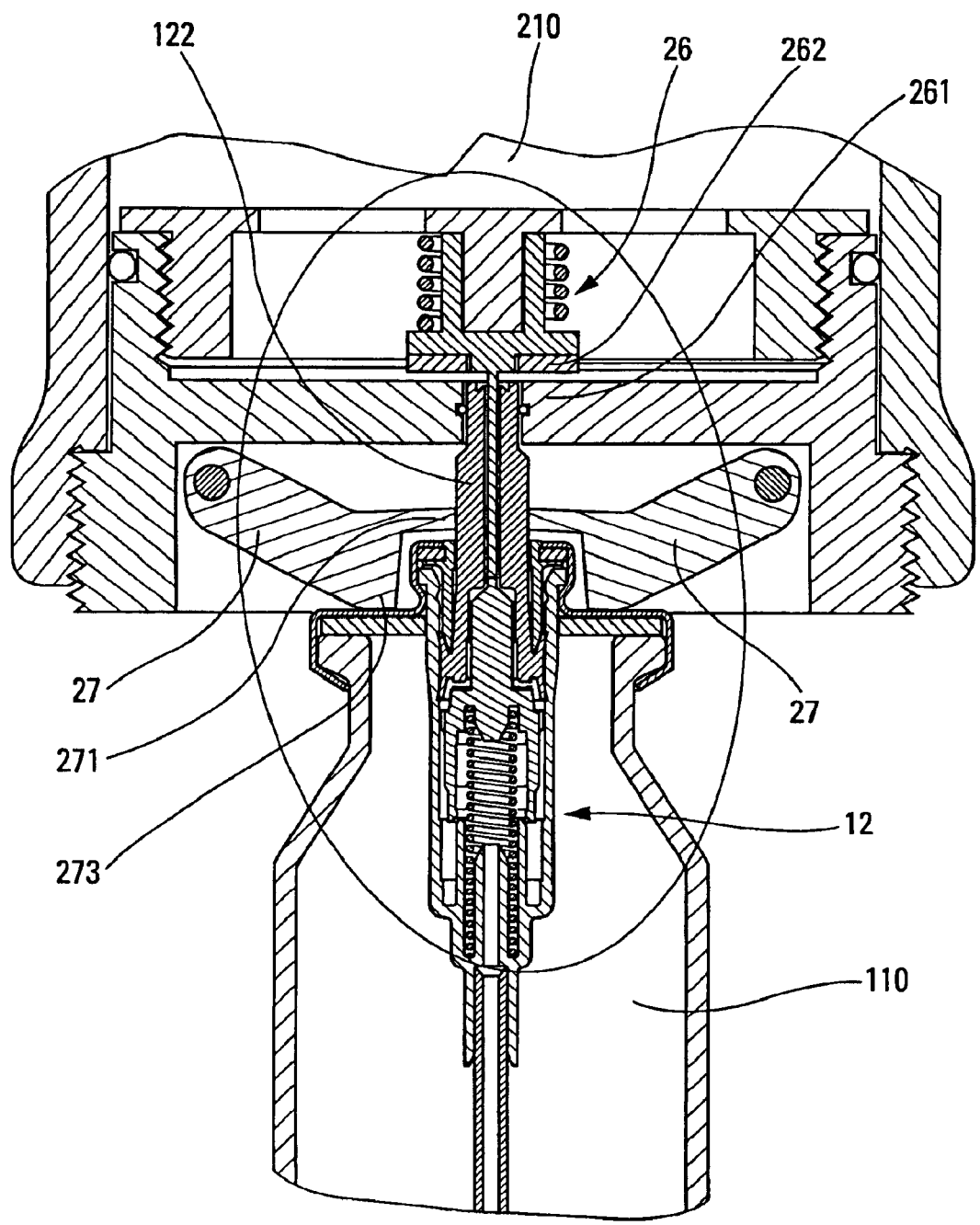
FIGS. 4a and 4b are views similar to FIGS. 2a and 2b during filling.
Figure 4B:
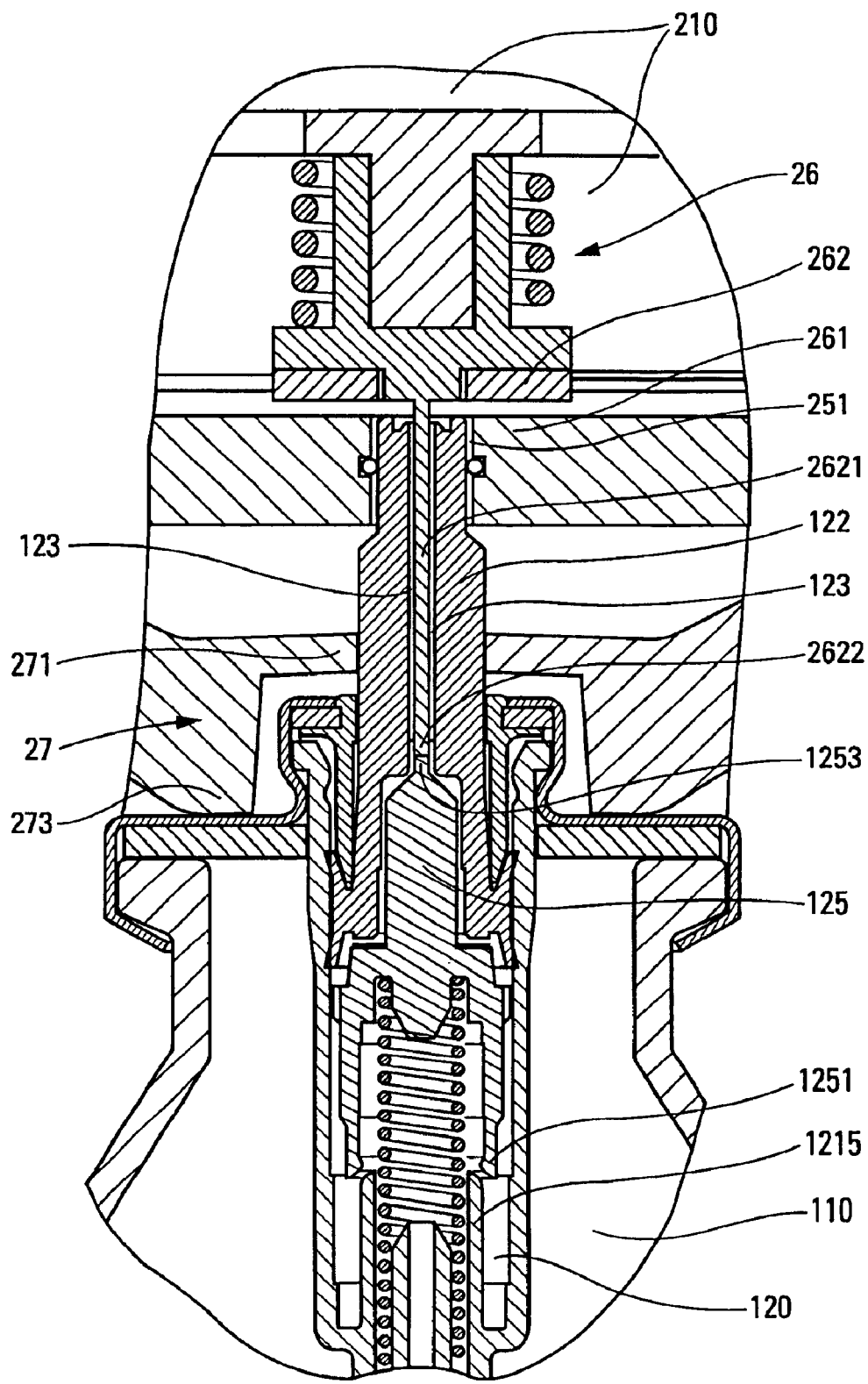

When the dispenser 1 continues to be pressed towards the dispenser 2, the position shown in FIGS. 3a and 3b is reached. The jaws 271 are now clamped around the actuator rod 122. The bearing surfaces 273 are in bearing contact against the crimping ring 13. The top end of the actuator rod 122 is engaged further into the supply orifice 251. The thrust end 2622 of the pin 2621 is in bearing contact against the tip 1253 of the valve part 125. The thrust of the pin 2621 against the valve part 125 is also sufficient to lift the movable member 262 of the supply valve 26 off its valve seat 261. A supply passage is thus created, which enables fluid stored in the reservoir 210 to pass into the outlet channel 123. It should not be forgotten that the fluid stored in the supply reservoir 210 is at a pressure that is substantially equal to or less than atmospheric pressure. As a result, the fluid can flow into the outlet channel 123 substantially without pressure. At this stage, it should be noted that the outlet valve 1225, 1252 is closed. It is possible to open the supply valve 26 while the outlet valve 1225, 1252 is closed, by calibrating the spring of the supply valve 26 to be weaker than the return spring 127 of the pump 12. Thus, it is the spring of the supply valve 26 which is compressed first, thereby enabling the supply valve 26 to open before the outlet valve 1225, 1252 opens.

By then exerting greater pressure on the dispenser 1 towards the source dispenser 2, the top end of the actuator rod 122 penetrates further into the supply opening 251. Given that the supply valve 26 has already been opened, this additional pressure has the effect of pushing the valve part 125 so as to open the outlet valve. Fluid communication is thus established between the two reservoirs 210 and 110. Not only are the supply valve 26 and the outlet valve open, but so too is the inlet valve 1251, 1215. The high level of suction existing inside the reservoir 110 becomes applied to the fluid in the source reservoir 210 which is at a pressure that is substantially equal to or slightly less than atmospheric pressure. As a result, fluid from the source reservoir 210, which is already present in the outlet channel 123 as a result of the supply valve 26 already being open, is sucked into the reservoir 110 through the pump 12, or more precisely through the outlet channel 123, the open outlet valve, the pump chamber 120, the open inlet valve, and the inlet of the pump possibly provided with a dip tube. The reservoir 110 is thus filled with sucked-in fluid until the pressures inside the two reservoirs 110 and 210 reach equilibrium. By selecting a source reservoir 210 having a capacity that is significantly greater than the capacity of the reservoir 110 to be filled, the reservoir 110 can be filled completely. It should also be noted that during the above filling step, the jaws 271, which are engaged on the rod 122, are displaced upwards slightly, thereby generating light traction on the actuator rod 122. In any case, even without light traction, it is preferable to hold the actuator rod 22 in place, i.e. in fixed or static manner relative to the body 121. As a result of the high level of suction which exists inside the reservoir 110, the actuator rod 122 tends to be sucked into the body when the outlet valve is opened by the pin 2621. Thus would have the unfortunately consequence of immediately closing the inlet valve, thereby making it impossible for filling to take place. One purpose of blocking the actuator rod 122 is therefore to keep the inlet valve open. Optional light upward traction has the advantageous consequence of increasing the flow section for the fluid coming from the source reservoir 210. Thus, head losses are smaller and filling is quicker and more complete.

Once the filling operation is complete, it suffices to remove the actuator rod from the pin 2621 and from between the jaws 271. Removal firstly causes the outlet valve of the pump 12 to close, and secondly causes the supply valve 26 to close. Thus, the two reservoirs 110 and 210 are once again isolated from the outside. The user has only to put the actuator head back into place on the top end of the actuator rod. After emptying the reservoir 110 by actuating the pump 12, the dispenser 1 can be refilled again in the manner described above, by using an external source 2 in which the fluid stored inside the source reservoir is not under pressure.

What is claimed is:

1. A method of filling a reservoir of a fluid dispenser, the dispenser comprising:

a reservoir designed to contain a fluid at a pressure that is substantially equal to or less than atmospheric pressure; and a pump associated, in sealed manner, with the reservoir, so as to extract fluid from the reservoir, the pump being of the airless type so that the pressure inside the reservoir reduces as the amount of fluid extracted by the pump increases, said pump including an inlet valve and an outlet valve, the inlet valve communicating with the reservoir, and the outlet valve communicating with an outlet channel, the inlet valve communicating with the outlet valve via a pump chamber, said method comprising:

a prior step of emptying the reservoir by using the pump to extract the fluid so that suction is created in the reservoir;

a step of supplying fluid externally, said step consisting in supplying the outlet channel with fluid coming from an external source; and an opening step consisting in opening the outlet valve, while holding the inlet valve open, so that the suction existing in the reservoir sucks fluid from the source through the outlet channel, the open outlet valve, the pump chamber, and the open inlet valve, and into the reservoir.

2. A filling method according to claim 1, in which the fluid coming from the external source is supplied to the outlet channel at a pressure that is substantially equal to or less than atmospheric pressure.

3. An external fluid-filler source for a fluid dispenser, the dispenser comprising:

a reservoir designed to contain a fluid at a pressure that is substantially equal to or less than atmospheric pressure; and a pump associated, in sealed manner, with the reservoir, so as to extract fluid from the reservoir, the pump being of the airless type so that the pressure inside the reservoir reduces as the amount of fluid extracted by the pump increases, said pump including an inlet valve and an outlet valve, the inlet valve communicating with the reservoir, and the outlet valve communicating with an outlet channel, the inlet valve communicating with the outlet valve via a pump chamber, the external source comprising:

a supply of fluid;

a fluid-supplying orifice designed to be connected to the outlet channel of the dispenser;

a supply valve disposed between the supply and the supply orifice, said supply valve being urged into its open position when the supply orifice is connected to the outlet channel of the dispenser, said supply valve including a movable member bearing selectively in leaktight manner on a valve seat.

4. A source according to claim 3, in which the fluid contained in the supply of the source is at a pressure that is substantially equal to or slightly less than atmospheric pressure, so that the fluid coming from the supply orifice is sucked into the reservoir of the dispenser by the suction which exists therein.

5. A source according to claim 3, including opening means that are capable of opening the outlet valve of the dispenser.

6. A source according to claim 5, in which the opening means also co-operate with the supply valve so as to open it before opening the outlet valve.

7. A source according to claim 6, in which the opening means comprise a pin defining a connection end secured to the movable member, and a free end for thrust purposes designed to be engaged in the outlet channel of the dispenser so as to open the outlet valve.

8. A source according to claim 3, the outlet channel of the dispenser being formed by an actuator rod that is axially displaceable in a pump body, the rod supporting a piston that is capable of varying the working volume of the pump chamber, blocking means being provided in the source so as to block the actuator rod relative to the pump body.

9. A source according to claim 8, in which the blocking means include at least two hinged jaws between which the actuator rod is designed to be held in clamped manner.

10. A source according to claim 9, in which the blocking means include a lever system that is capable of exerting traction which urges the rod out from the body, while said rod is already being held by the jaws.

11. A source according to claim 9, in which the blocking means include at least two hinged arms, each presenting a fixed end and a jaw-forming free end, the jaws being disposed in such a manner as to define a central housing of size that varies as the jaws are displaced by pivoting the arms, each of the arms also forming a bearing surface designed to come into bearing contact on a fixed element of the dispenser, pivoting the arms in the direction for reducing the size of the central housing, while the rod is inserted in said housing, causes the jaws to clamp onto the rod, and brings the bearing surfaces into contact with the fixed element in such a manner as to exert traction on the rod by means of the jaws, urging the rod out from the body.

12. A source according to claim 9, in which the movable member of the supply valve includes a pin designed to be inserted in the outlet channel so as to open the outlet valve, the pin extending in central and axial manner between the jaws of the blocking means so as to guide the outlet channel axially around the pin.

13. A source according to claim 1, in which the external source is constituted by another fluid dispenser also including a reservoir and a pump.

14. A source according to claim 3, in which the inlet valve comprises a valve seat and a movable member, the outlet valve comprises a valve seat and a movable member, the movable members being formed by a valve part so that the movable members are constrained to move together, it thus being possible to open the inlet and outlet valves simultaneously.

15. A dispenser and filler system comprising:

a fluid dispenser comprising:

a reservoir designed to contain a fluid at a pressure that is substantially equal to or less than atmospheric pressure; and a pump associated, in sealed manner, with the reservoir, so as to extract fluid from the reservoir, the pump being of the airless type so that the pressure inside the reservoir reduces as the amount of fluid extracted by the pump increases, said pump including an inlet valve and an outlet valve, the inlet valve communicating with the reservoir, and the outlet valve communicating with an outlet channel, the inlet valve communicating with the outlet valve via a pump chamber; and an external filler source according to claim 3.

* * * * *